(12) United States Patent
Ke et al.

(10) Patent No.: US 12,258,568 B2
(45) Date of Patent: Mar. 25, 2025

(54) HIGH-EFFICIENCY ARTIFICIAL COMBINED RHIZOSPHERE NITROGEN FIXATION SYSTEM

(71) Applicant: BEIJING GREENBIO-TECH CO., LTD, Beijing (CN)

(72) Inventors: Xiubin Ke, Beijing (CN); Min Lin, Beijing (CN); Yongliang Yan, Beijing (CN); Yuhua Zhan, Beijing (CN); Wei Lu, Beijing (CN)

(73) Assignee: BEIJING GREENBIO-TECH CO., LTD, Beijing (CN)

( * ) Notice: Subject to any disclaimer, the term of this patent is extended or adjusted under 35 U.S.C. 154(b) by 96 days.

(21) Appl. No.: 17/926,989

(22) PCT Filed: Jul. 6, 2020

(86) PCT No.: PCT/CN2020/100411
§ 371 (c)(1),
(2) Date: Nov. 21, 2022

(87) PCT Pub. No.: WO2021/232551
PCT Pub. Date: Nov. 25, 2021

(65) Prior Publication Data
US 2023/0193306 A1    Jun. 22, 2023

(30) Foreign Application Priority Data
May 21, 2020  (CN) .......... 202010435008.6

(51) Int. Cl.
*C12N 15/74* (2006.01)
*C12N 15/82* (2006.01)

(52) U.S. Cl.
CPC ......... *C12N 15/8243* (2013.01); *C12N 15/74* (2013.01); *C12N 2510/00* (2013.01)

(58) Field of Classification Search
CPC ................................................ C12N 15/8243
See application file for complete search history.

(56) References Cited

FOREIGN PATENT DOCUMENTS

| CN | 101298600 A | 11/2008 |
|----|-------------|---------|
| CN | 107119000 A | 9/2017 |
| CN | 108602729 A | 9/2018 |
| CN | 110573623 A | 12/2019 |
| WO | 2019213939 A1 | 11/2019 |

OTHER PUBLICATIONS

Goyal et al., 2021, Molecular Biology in the Improvement of Biological Nitrogen Fixation by Rhizobia and Extending the Scope to Cereals, Microorganisms 9(1): 125: 1-24. (Year: 2021).*
Mahmud et al., 2020, Current Progress in Nitrogen Fixing Plants and Microbiome Research, Plants 9:97: 1-17. (Year: 2020).*
Sun Shuai-Xin, et al., Generation of Tn5 insertion mutations in nitrogen-fixing bacterium Kosakonia radicincitans GXGL-4A associated with maize, Microbiology China, 2018, pp. 1711-1718, vol. 45, No. 8.
Sharon Perrone, et al., Nitrogen fixation and productivity of winter annual legume cover crops in Upper Midwest organic cropping systems, Nutr Cycl Agroecosyst.

* cited by examiner

*Primary Examiner* — Bratislav Stankovic
(74) *Attorney, Agent, or Firm* — Bayramoglu Law Offices LLC

(57) ABSTRACT

An artificial combined rhizosphere nitrogen fixation system includes a recombinant nitrogen-fixing engineering bacterium, which is transformed with genes for encoding a nitrogen fixation activator Neb and an ammonium transporter amtR, and a recombinant plant, which is transformed with a gene for encoding an ammonium-affiliated protein Ham. The coupling of the functions of the above two is achieved through a seed-coated inoculation at a rhizosphere of a crop.

10 Claims, 4 Drawing Sheets
Specification includes a Sequence Listing.

HIGH-EFFICIENCY ARTIFICIAL COMBINED RHIZOSPHERE NITROGEN FIXATION SYSTEM

CROSS REFERENCE TO THE RELATED APPLICATIONS

This application is the national phase entry of International Application No. PCT/CN2020/100411, filed on Jul. 6, 2020, which is based upon and claims priority to Chinese Patent Application No. 202010435008.6, filed on May 21, 2020, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy is named GBDGG076-PKG_Sequence_Listing.txt, created on Nov. 16, 2022, and is 3,805 bytes in size.

TECHNICAL FIELD

The present disclosure belongs to the technical field of synthetic biology and specifically relates to a high-efficiency artificial combined rhizosphere nitrogen fixation system and its use.

BACKGROUND

Nitrogen fertilizer inputs are necessary for agricultural producers to achieve high yields, but the current nitrogen utilization efficiency is generally not high, resulting in the overuse of nitrogen fertilizers. A plant rhizosphere is an active interface for material exchange between the soil and a plant and is also the main activity area for an interaction between a host plant and a microorganism. A combined nitrogen fixation system is widely found in the rhizospheres of non-leguminous crops such as *Oryza sativa* L. and *Zea mays* L. However, a natural combined nitrogen fixation system has many defects, such as severe limitations due to rhizosphere biological stress, low nitrogen fixation efficiency, weak stress resistance and ammonia resistance of wild nitrogen-fixing mycorrhiza, and weak nitrogen utilization capacity of traditional crop roots.

Synthetic biology is an interdisciplinary area with the concepts of systematic design and engineering construction and is a development frontier of the new generation of disruptive biotechnologies. In synthetic biology, the "bottom-up" design from elements to modules and then to systems is realized in a living host or an in vitro system for transcription and translation as a chassis by using the concept of engineering design. Biomacromolecules such as DNA, RNA, and proteins of a biological system are used as candidates of "components" for artificial designs and intelligent transformations Biological functions such as transcriptional regulation and metabolic regulation are used to link these artificial components to create artificial "functional modules", "regulatory loops", or "intelligent systems" to achieve new biological functions that are more efficient, energy-saving, or environmentally friendly.

The traditional research on enhancing plant nitrogen utilization efficiency mainly focuses on the following two technical aspects: 1. Through performance improvement of a plant chassis, an efficient nitrogen utilization functional module is artificially designed to enhance the affinity of a plant for nitrogen. 2. Artificially-designed modules such as a nitrogen-fixing bacteria nitrogen fixation module and an ammonia-resistant ammonium secretion module are used to improve the nitrogen fixation efficiency of nitrogen-fixing microorganisms in the rhizosphere, such that the nitrogen-fixing microorganisms provide a plant with increased biologically-fixed nitrogen.

However, the traditional method has many shortcomings such as a long research cycle. In addition, the improved technologies for microorganisms and plants and applications thereof are relatively independent. Therefore, the establishment of a brand-new artificial combined rhizosphere nitrogen fixation system based on synthetic biology techniques is of great significance for improving nitrogen fertilizer utilization rate and reducing the dependence on nitrogen fertilizers in agricultural production.

SUMMARY

The present disclosure is intended to establish a brand-new artificial combined rhizosphere nitrogen fixation system.

In the artificial combined rhizosphere nitrogen fixation system of the present disclosure, based on synthetic biology techniques, the following two brand-new functional modules are artificially designed and constructed: a nitrogen-fixing and ammonium-secreting gene module constructed by a nitrogen-fixing microbial chassis and an efficient nitrogen utilization module constructed by a non-leguminous plant chassis. The above two modules are functionally coupled through coated seed inoculation at a rhizosphere of a crop.

That is, a recombinant nitrogen-fixing engineering bacterium (the nitrogen-fixing microbial chassis) carrying the nitrogen-fixing and ammonium-secreting gene module is inoculated into a recombinant plant carrying the efficient nitrogen utilization module (the efficient nitrogen utilization plant chassis) to achieve the coupling of the functions of the two modules.

The nitrogen-fixing and ammonium-secreting gene module includes a nitrogen fixation activator Neb (encoded by a DNA sequence shown in SEQ ID NO: 1) functional module and an amtR (encoded by a DNA sequence shown in SEQ ID NO: 2) ammonium transport module that are artificially designed.

The efficient nitrogen utilization module of the plant chassis is an artificially-designed ammonium-affiliated protein Ham functional module. The present disclosure designs and constructs three plant chassis, specifically including:
  recombinant *Zea mays* L. carrying a gene Ham and a gene bar;
  recombinant *Oryza sativa* L. carrying a gene Ham and a gene hyg; and
  recombinant *Triticum aestivum* L. carrying a gene Ham and a gene NPT II.

Ham is a gene encoding the ammonium-affiliated protein Ham, which is first synthesized by the present disclosure and has a nucleotide sequence shown in SEQ ID NO: 3.

A construction method of the artificial combined rhizosphere nitrogen fixation system is provided, including:
  1) preparing a nitrogen-fixing and ammonium-secreting module and introducing the nitrogen-fixing and ammonium-secreting module into a nitrogen-fixing microorganism to obtain a recombinant microorganism carrying the nitrogen-fixing and ammonium-secreting module;
  2) preparing an efficient nitrogen utilization module and introducing the efficient nitrogen utilization module into a plant to obtain a recombinant plant carrying the efficient nitrogen utilization module; and 3) conducting inoculations such as seed coating at a rhizosphere of a crop to achieve the functional coupling of the ammonium-secreting module on the nitrogen-fixing microbial chassis and the efficient nitrogen utilization module on the plant chassis.

A method for using the artificial combined rhizosphere nitrogen fixation system of the present disclosure is provided, including inoculating a recombinant nitrogen-fixing microorganism carrying the nitrogen-fixing and ammonium-secreting module into a rhizosphere of a recombinant plant carrying the efficient nitrogen utilization module.

Thus, the present disclosure constructs the following artificial combined rhizosphere nitrogen fixation systems:
a neb+amtR ammonium-secreting engineering bacterium and a Ham+bar *Zea mays* L. strain;
a neb+amtR ammonium-secreting engineering bacterium and a Ham+hyg *Oryza sativa* L. strain; and
a neb+amtR ammonium-secreting engineering bacterium and a Ham+NPT II *Triticum aestivum* L. strain.

The growth amount and biologically-fixed nitrogen amount of a plant are measured to evaluate the growth promotion effect and nitrogen fixation efficiency, and evaluation results show that the artificial combined rhizosphere nitrogen fixation system provided by the present disclosure has a significant nitrogen fixation effect.

Specifically, the present disclosure conducts the following work:

1. Construction of a Microbial-Efficient Nitrogen-Fixing and Ammonium-Secreting Gene Module

*Pseudomonas stutzeri* (*P. stutzeri*) A1501 is used as a model combined nitrogen-fixing bacterium to construct an efficient nitrogen-fixing and ammonium-secreting microbial chassis. An efficient ammonium transporter gene amtR which is artificially designed is with a high ammonium-resistant promoter. Under nitrogen-limited conditions, the ammonium-affiliated protein amtR transports extracellular ammonium into cells.

Through the following artificially-designed functional module, an engineering bacterium for improving the ammonium resistance and ammonium-secreting ability of nitrogenase is constructed:
a nitrogen fixation-activating Neb functional module is artificially designed for wild-type (WT) A1501, and the Neb functional module and the amtR functional module are transformed into a WT bacterial strain to obtain a nitrogen-fixing and ammonium-secreting engineering bacterium.

2. Construction of Three Efficient Nitrogen Utilization Modules Based on Different Plant Chassis 1) Construction of an Efficient Nitrogen Utilization for *Zea mays* L. Strain With *Zea mays* L. as a model plant, a synthetic target gene is used to construct an efficient nitrogen utilization *Zea mays* L. chassis.

A specific process is as follows: The target gene is constructed on an expression vector pCAMBIA 3300-bar (purchased from Biovector Science Lab, Inc), and with *Zea mays* L. Hill as a receptor, *Agrobacterium tumefaciens* (*A. tumefaciens*)-mediated embryo transformation is conducted. Herbicide screening, polymerase chain reaction (PCR), reverse transcription-polymerase chain reaction (RT-PCR), Southern blot, and other technologies are used to determine whether the target gene is inserted into a genome of *Zea mays* L., stably expressed, and steadily inherited over multiple generations to obtain the efficient nitrogen utilization *Zea mays* L. strain.

The target gene used for the efficient nitrogen utilization *Zea mays* L. strain includes a target gene Ham via the synthetic ammonium-affiliated protein and a glufosinate-resistant screening gene bar.

2) Construction of an Efficient Nitrogen Utilization *Oryza sativa* L. Strain

With *Oryza sativa* L. as a model plant, a synthetic target gene is used to construct an efficient nitrogen utilization *Oryza sativa* L. chassis.

A specific process is as follows: The target gene is constructed on an expression vector pCXK1301-hyg (purchased from Biovector Science Lab, Inc), and with *Oryza sativa* L. IR8 as a receptor, *A. tumefaciens*-mediated embryo transformation is conducted. Antibiotic screening, PCR, RT-PCR, Southern blot, and other technologies are used to determine whether the target gene is inserted into a genome of *Oryza sativa* L. stably expressed and steadily inherited over multiple generations to obtain the efficient nitrogen utilization *Oryza sativa* L. strain.

The target gene used for the efficient nitrogen utilization of *Oryza sativa* L. strain includes a target gene Ham for the synthetic ammonium-affiliated protein and a hygromycin-resistant screening gene hyg.

3) Construction of an Efficient Nitrogen Utilization *Triticum aestivum* L. Strain With *Triticum aestivum* L. as a model plant, a synthetic target gene is used to construct an efficient nitrogen utilization *Triticum aestivum* L. chassis.

A specific process is as follows: The target gene is constructed on an expression vector pCAMBIA1301-35S-NPT II (purchased from Biovector Science Lab, Inc), and with *Triticum aestivum* L. 411 as a receptor, *A. tumefaciens*-mediated embryo transformation is conducted. Antibiotic screening, PCR, RT-PCR, Southern blot, and other technologies are used to determine whether the target gene is inserted into a genome of *Triticum aestivum* L. stably expressed and steadily inherited over multiple generations to obtain the efficient nitrogen utilization *Triticum aestivum* L. strain.

The target gene used for the efficient nitrogen utilization of *Triticum aestivum* L. strain includes a target gene Ham for the synthetic ammonium-affiliated protein and a kanamycin-resistant screening gene NPT II.

3. Functional Adaptation Between the Microorganism and the Plant Chassis and Investigation of their Field Use The above ammonium-secreting engineering bacterium is combined with each of the efficient nitrogen utilization *Zea mays* L., *Oryza sativa* L., and *Triticum aestivum* L. to obtain the following three artificial combined rhizosphere nitrogen fixation systems (FIG. 1):
a neb+amtR ammonium-secreting engineering bacterium and a Ham+bar *Zea mays* L. strain;
a neb+amtR ammonium-secreting engineering bacterium and a Ham+hyg *Oryza sativa* L. strain; and
a neb+amtR ammonium-secreting engineering bacterium and a Ham+NPT II *Triticum aestivum* L. strain.

The rhizosphere nitrogen fixation efficiency and plant growth promotion effect of each of the three artificial combined rhizosphere nitrogen fixation systems are investigated and evaluated by measuring the plant growth and biologically-fixed nitrogen amounts of the three artificial combined rhizosphere nitrogen fixation systems under greenhouse conditions.

Results show that the rhizosphere nitrogen fixation efficiency and plant growth promotion effect of each of the three artificial combined rhizosphere nitrogen fixation systems are significantly higher than that of a control system.

In the present disclosure, based on synthetic biology techniques, a nitrogen-fixing and ammonium-secreting module of a microorganism and an efficient nitrogen utilization module of a plant are constructed, and the functional adaptation of the two modules is completed in a nitrogen-fixing bacterial chassis and the Zea mays L., Oryza sativa L., and Triticum aestivum L. chassis, such that the microbial nitrogen-fixing and ammonium-secreting gene circuit and the efficient nitrogen utilization module based on a plant chassis are functionally coupled to form a brand-new artificial combined rhizosphere nitrogen fixation system. Compared with the control system, the brand-new artificial combined rhizosphere nitrogen fixation system has prominent nitrogen fixation efficiency and growth promotion effect and exhibits the potential to reduce fertilizer consumption and increase the yield, which provides a new method for solving problems such as low fixation efficiency of nitrogen and low utilization in an agricultural production system. This method also overcomes the problem that the traditional method has a long research cycle and cannot achieve the genetic modification between a plant and a microorganism. Information in the Sequence Listings SEQ ID NO: 1: a DNA sequence of the gene neb;
SEQ ID NO: 2: a DNA sequence of the gene amtR; and
SEQ ID NO: 3: a DNA sequence of the gene ham.

BRIEF DESCRIPTION OF THE DRAWINGS

In FIG. 2 to FIG. 4:
WT bacterial strain: WT P. stutzeri A1501;
nitrogen-fixing gene-mutant strain: nifH gene-deleted mutant strain;
ammonium-secreting engineering bacterial strain: Neb+amtR ammonium-secreting engineering bacterium; and
n.d.: not detected.

DETAILED DESCRIPTION OF THE EMBODIMENTS

Figure 1:
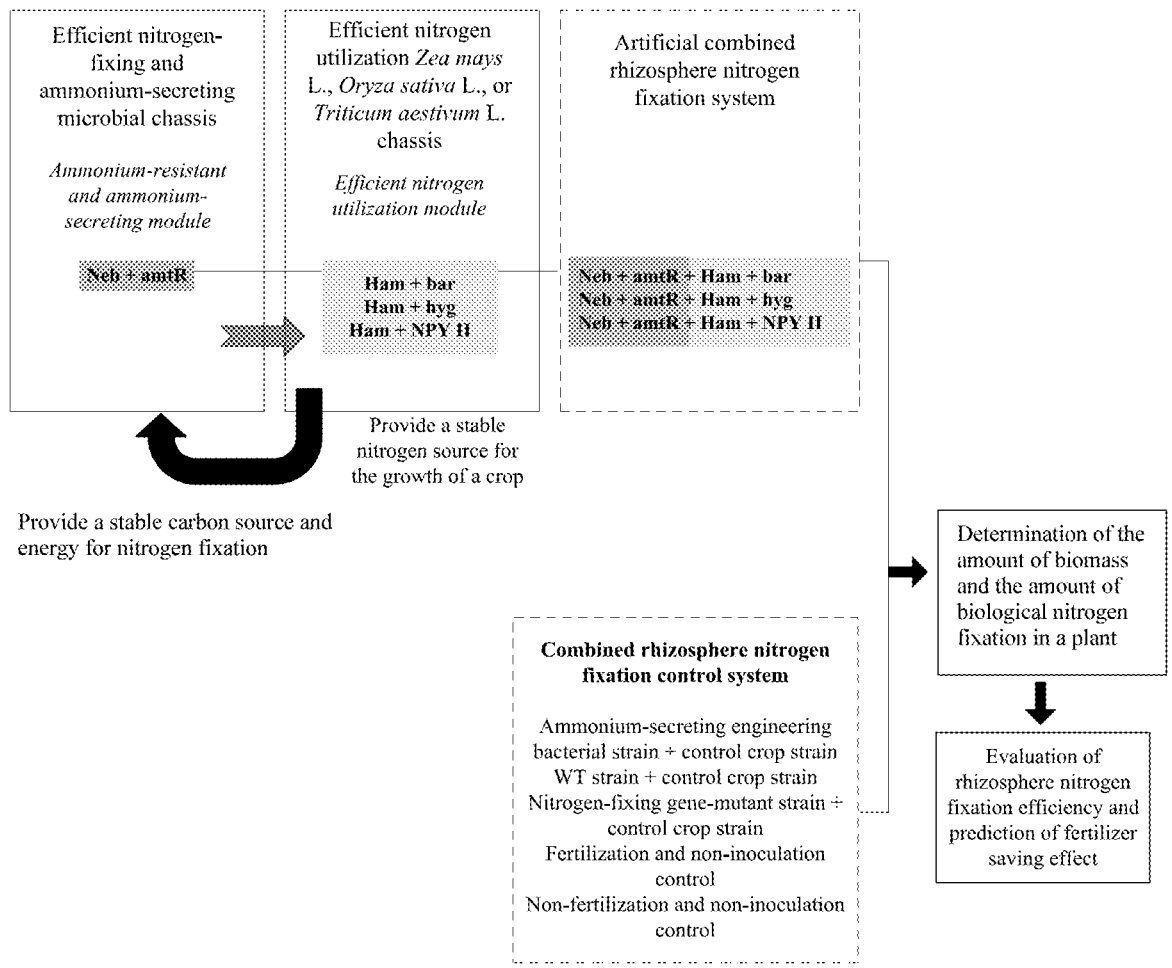
FIG. 1 is a schematic diagram of an artificial combined rhizosphere nitrogen fixation system, where the efficient nitrogen-fixing and ammonium-secreting microbial chassis includes a Neb+amtR ammonium-secreting engineering bacterium. The efficient nitrogen utilization crop chassis includes a Ham+bar Zea mays L. chassis, a Ham+hyg Oryza sativa L. chassis, and a Ham+NPY II Triticum aestivum L. chassis.

The present disclosure will be further described below with reference to specific examples. It should be understood that these examples are provided only to describe the method of the present disclosure, rather than to limit the scope of the present disclosure. If specific experimental conditions are not specified in an example, the example is conducted in accordance with the general conditions well known to those skilled in the art.

Example 1 Preparation of a Neb+amtR Ammonium-Secreting Engineering Bacterium

1. Construction of an amt gene-deleted mutant strain in nitrogen-fixing P. stutzeri A1501:

An upstream homologous fragment of a target gene, a chloramphenicol resistance box gene, and a downstream homologous fragment of the target gene were fused into a fusion fragment with a size of about 4.1 kb through fusion PCR, and the fusion fragment was subjected to double enzyme digestion with BamH I and Hind III and ligated to a suicide vector pk18mobsacB. A constructed suicide recombinant plasmid was introduced into the WT strain A1501 through three-parent bending, and the suicide plasmid was integrated into a chromosome of the strain through homologous recombination with a gene on the chromosome. A single-crossover strain was obtained through resistance screening and PCR verification, and according to the lethal characteristics of the amt gene under 10% sucrose selection, a single-crossover clone verified by PCR was coated on chloramphenicol-resistant LB plates including 10% sucrose according to dilution gradients of $10^{-3}$, $10^{-4}$, and $10^{-5}$ to conduct double crossover screening. PCR verification was conducted to obtain amt-deleted mutant strain Aamt as a target gene.

2. Construction of a recombinant strain by transforming genes Neb and amtR in nitrogen-fixing P. stutzeri A1501: Intact Neb and amtR DNA fragments each were acquired through PCR amplification, subjected to enzyme digestion with BamHI and HindIII, and inserted into multiple cloning sites (MCSs) of a broad-host-range expression vector pLAFR3. Resulting neb and amtR expression vectors were transformed into an Escherichia coli (E. coli) competent cell Trans109 to obtain a tetracycline-resistant recombinant expression strain E. coli Trans109 (pneb+amtR). The constructed E. coli Trans109 (pneb+amtR) donor plasmid was also introduced into the amt-deleted mutant strain through three-parent bending.

Example 2 Determination of a Nitrogen Fixation Effect of the Neb+amtR Ammonium-Secreting Engineering Bacterium 1. Experimental Purpose: Investigating the Nitrogenase Activity and Ammonium-Secreting Ability of Engineering Bacteria (Growth Curve, Nitrogenase Activity, and Ammonium-Secreting Characteristics of Nitrogen-Fixing Strains)
2. Experimental Subjects:
Control strain: WT P. stutzeri A1501;
nitrogen-fixing gene-mutant strain: nifH gene-deleted mutant strain; and ammonium-secreting engineering bacterial strain: Neb+amtR ammonium-secreting engineering bacterium.
3. Experimental Methods:
The nitrogenase activity was determined for the nitrogen-fixing strains as follows:
The WT strain, the ammonium-secreting engineering bacterial strain, and the nifH gene-deleted mutant strain each were picked and inoculated in an LB liquid medium with a corresponding antibiotic and cultivated overnight under shaking at 30° C. and 220 r/min. The resulting cell suspension was centrifuged at 4° C. and 4,000 r/min for 10 min to collect the resulting bacterial cells. The collected bacterial cells were washed twice with a 0.85% NaCl solution and transferred to an A15 medium. The initial $OD_{600}$ of the resulting cell suspension was adjusted to 0.1, and the cells were cultivated under shaking at 30° C. and 200 r/min, during which a sample was taken every 2 h to determine the $OD_{600}$ of the strain. A growth curve was plotted with time (h) as an abscissa axis and $OD_{600}$ as an ordinate axis.

The nitrogenase activity of each of the strains was determined by acetylene reduction, and a specific process was as follows:

10 mL of a bacterial solution obtained after cultivation overnight was taken and centrifuged at 6,000 rpm/min for 10 min. The resulting bacterial precipitate was washed twice with a 0.85% NaCl solution. 1 mL of a bacterial solution with $OD_{600}$ of 1.0 was taken and transferred to a triangular flask with 9 mL of an A15 nitrogen-free medium, where the resulting cell suspension had an initial $OD_{600}$ of 0.1 and a volume of 10 mL. The triangular flask was covered with a rubber stopper, sealed, and argon was introduced for 4 min to expel air in the triangular flask. 0.5% oxygen and 10% acetylene were introduced into the triangular flask. 4 replicates were set for each group. The triangular flask was cultivated under shaking at 30° C. and 220 r/min. 250 µL of gas was extracted from the triangular flask with a microsampler every 2 h and injected into a gas chromatograph (SP-2305 gas chromatograph) to detect an ethylene content, and an ethylene peak area was recorded. The nitrogenase activity was calculated by the following formula: nitrogenase activity [nmol $C_2H_4$/(mg protein·h)]=area of an ethylene peak of a test strain×(volume of a gas phase in the triangular flask/injection amount)/area of a 1 nmol standard ethylene peak×bacterial protein concentration×reaction time. 4 replicates were set for each group.

The ammonium-secreting ability was determined for the nitrogen-fixing strains as follows:

A strain to be tested was inoculated into an LB liquid medium with a corresponding antibiotic and cultivated overnight. The resulting bacteria were collected through centrifugation, transferred to 10 mL of an A15 liquid medium with an initial $OD_{600}$ adjusted to 0.1, and cultivated under nitrogen fixation conditions for 72 h. The resulting supernatant was collected and tested by a microplate reader for an ammonium ion concentration. 4 replicates were set for each group.

Figure 2:
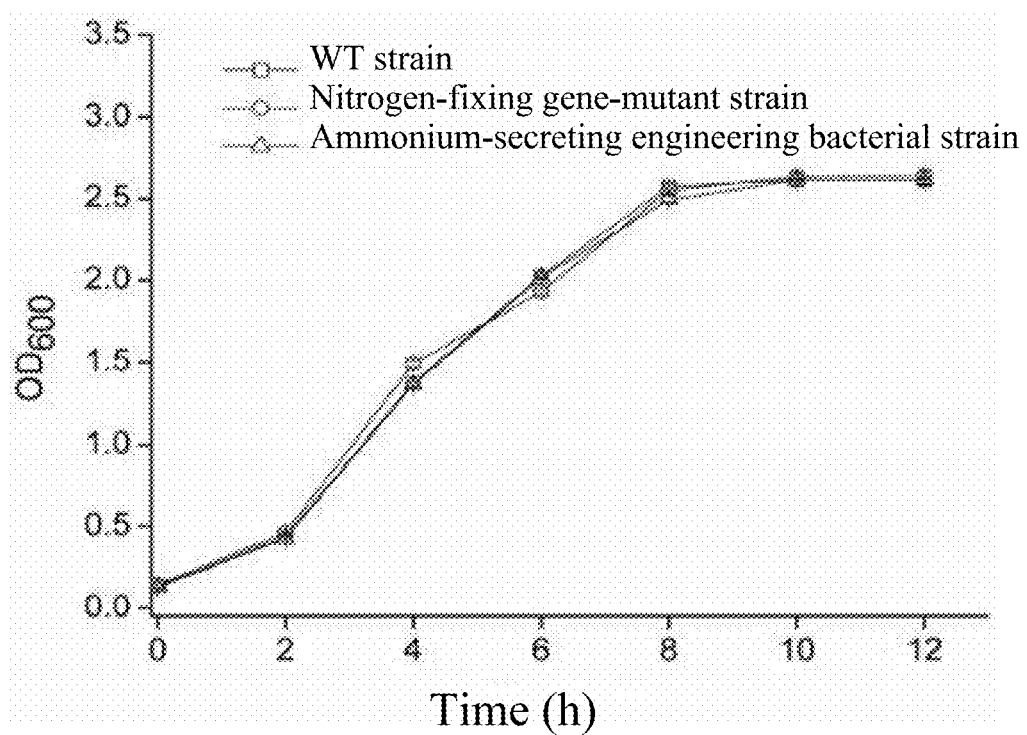
FIG. 2 shows growth curves of efficient nitrogen-fixing and ammonium-secreting microbial chassis.
Figure 3:
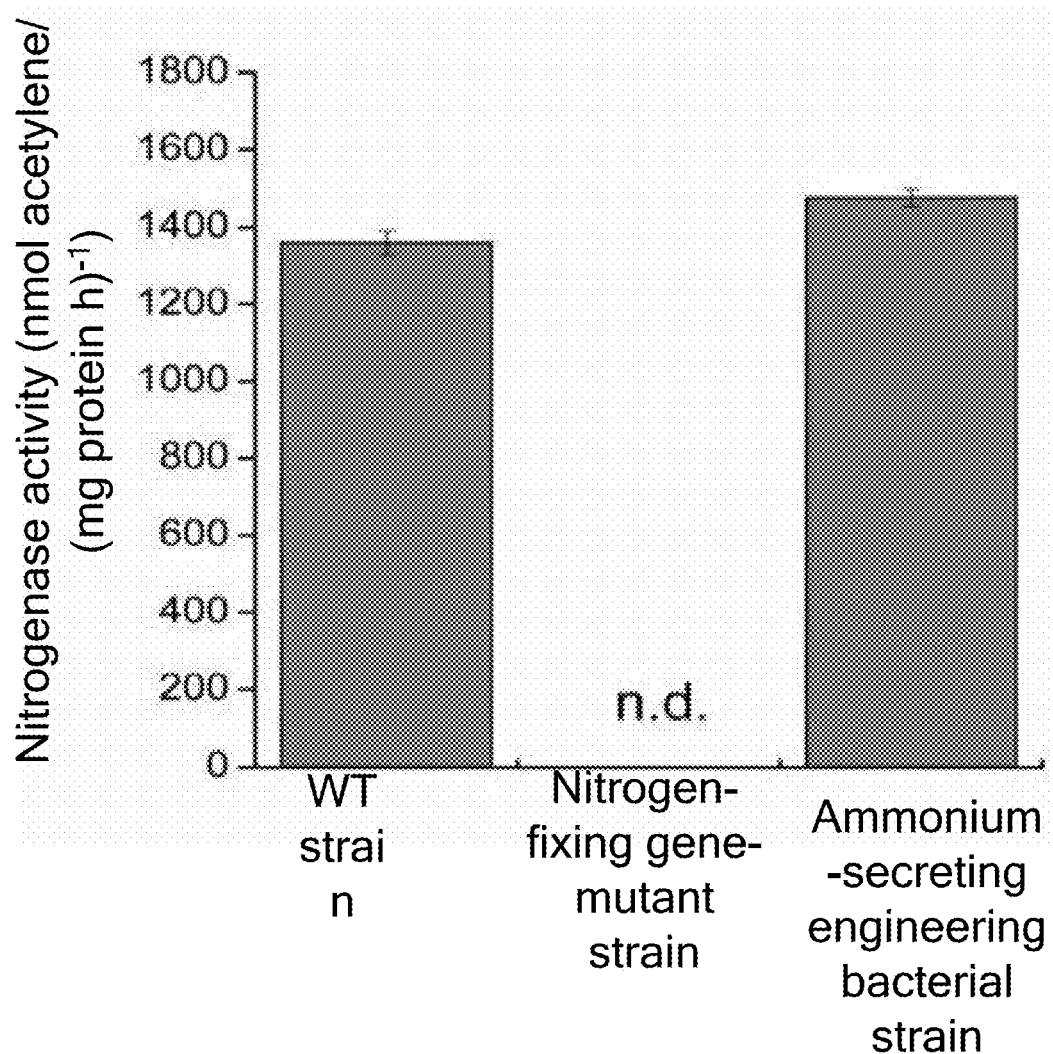
FIG. 3 shows nitrogenase activity characteristics of efficient nitrogen-fixing and ammonium-secreting microbial chassis.
Figure 4:
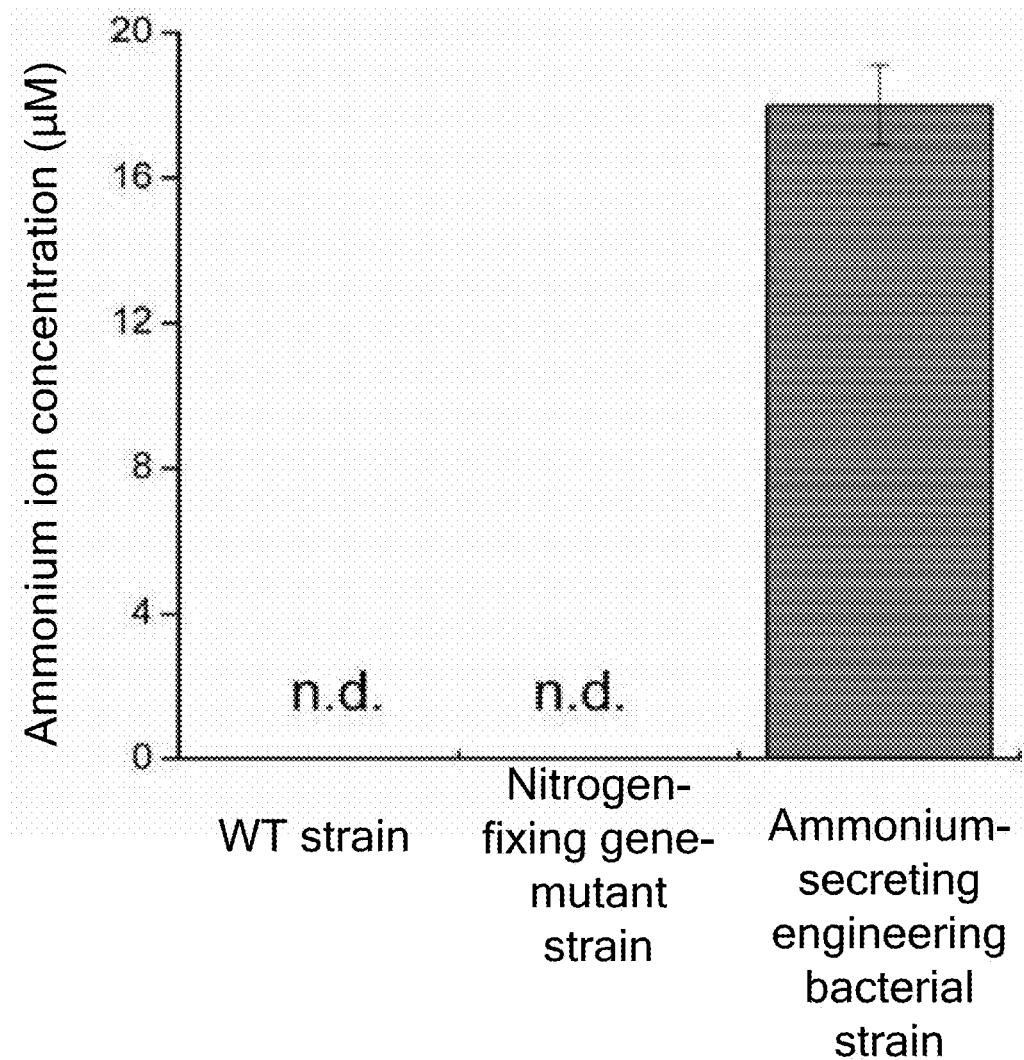
FIG. 4 shows the ammonium-secreting abilities of efficient nitrogen-fixing and ammonium-secreting microbial chassis.

4. Experimental Results:

The WT nitrogen-fixing *P. stutzeri*, the ammonium-secreting engineering bacterial strain, and the nifH gene-deleted mutant strain grew in substantially the same manner in the LB medium. All three entered a logarithmic growth phase at 2 h and reached a plateau stage at 8 h to 10 h (FIG. 2). Under nitrogen fixation conditions, the nitrogenase activity of the ammonium-secreting engineering bacterial strain reached 1,477 nmol acetylene/(mg protein h)$^{-1}$, which was slightly higher than the nitrogenase activity of the WT (FIG. 3). Under nitrogen fixation conditions, the extracellular ammonium ion concentration of the ammonium-secreting engineering bacterial strain reached 18 µM after being cultivated for 72 h (FIG. 4).

5. Experimental Conclusion:

The physiological activities of the ammonium-secreting engineering bacterial strain are normal, among which the nitrogenase activity and ammonium-secreting ability are optimal, and thus the ammonium-secreting engineering bacterial strain can be used for the subsequent construction of efficient combined nitrogen fixation systems.

Example 3 the Use Effect of an Efficient Combined Nitrogen Fixation System Constructed by the Ammonium-Secreting Engineering Bacterial Strain and *Zea mays* L. In the Field Experimental Method
(1) Determination of a Plant Growth Amount An experiment was conducted in a smart greenhouse in which the temperature and humidity could be controlled at all times. 5 treatment groups were set in the experiment (the ammonium-secreting engineering bacterial strain, the WT strain, the nifH gene-deleted mutant strain, 50 mg N of nitrogen application per kilogram of soil, and a treatment control without fertilization and inoculation). 2 *Zea mays* L. varieties were adopted (efficient nitrogen utilization strain and control strain), and 8 replicates were set for each group in the experiment. A total of 5×2×8=80 samples were set in this experiment.

*Zea mays* L. seeds were soaked and washed in sterile water for 30 min, soaked in a 5% NaClO solution for 1 min, treated in 75% ethanol for 2 min, and washed 5 times with sterile water. The seeds obtained after the surface sterilization were soaked for 30 min in various prepared bacterial suspensions and a sterilized WT suspension (a control without inoculation), respectively. The soaked *Zea mays* L. seeds were placed in plastic pots (inner diameter: 20 cm, and height: 20 cm) each filled with 2.5 kg of a soil substrate (Klasmann-Deilmann) with 4 seeds per pot and 8 replicates per group. 8 replicates were set for each group. After the emergence of *Zea mays* L. seedlings, the thinning was conducted to 2 seedlings/pot. The seedlings were managed in a growth cycle of *Zea mays* L. 60 days after the sowing, and the aboveground and underground growth amounts of *Zea mays* L. were measured.

Experimental Results:

On day 60 of the *Zea mays* L. growth cycle, aboveground and underground parts of a *Zea mays* L. plant were collected and tested for plant biomass, including plant height, plant weight, and root weight (Table 1). Data analysis showed that, compared with the fertilization and non-inoculation control systems, the combined nitrogen fixation system constructed by the Neb+amtR ammonium-secreting engineering bacterial strain and the Ham+bar *Zea mays* L. strain had a significantly-increased plant biomass.

The plant height, biomasses of aboveground and underground parts, and total biomass of a plant in this efficient nitrogen fixation system were significantly higher than that in the control (Table 1). The total biomass of the plant inoculated with the ammonium-secreting engineering bacterial strain was 7.2% higher than that of the fertilization treatment and 14.9% higher than that of the non-inoculation control, where the biomass of the aboveground part was 13.5% higher than that of the fertilization treatment and 19.0% higher than that of the non-inoculation control. The root weight was 1.2% higher than that of the fertilization treatment and 3.6% higher than that of the non-inoculation control.

An average plant height in the artificially-designed efficient nitrogen fixation system was significantly higher than that in the control system (Table 1). An average plant height of *Zea mays* L. inoculated with the ammonium-secreting engineering bacterial strain was 1.9% higher than that of the fertilization treatment and 4.7% higher than that of the non-inoculation control.

Experimental Conclusion:

The artificial combined nitrogen fixation system constructed by the efficient nitrogen-fixing and ammonium-secreting microbial chassis and the efficient nitrogen utilization plant chassis can significantly increase a plant's growth amount and exhibit the optimal growth promotion effect on Zea mays L.

(2) Determination of an Amount of Biological Nitrogen Fixation by a 15N Stable Isotope Dilution Method Experimental Results:

The nitrogen-fixing ability of nitrogen-fixing bacteria in the artificially-designed combined rhizosphere nitrogen fixation system was evaluated by the 15N dilution method (Table 2). Data analysis of the artificial combined nitrogen fixation system constructed by the Neb+amtR ammonium-secreting engineering bacterial chassis and the Ham+bar Zea mays L. chassis showed that, compared with the control system, the ammonium-secreting engineering bacteria significantly increased the total nitrogen content in a Zea mays L. plant, the percentage of nitrogen fixed from the air in a total nitrogen amount in a plant (biological nitrogen fixation efficiency), and an amount of biological nitrogen fixation.

In the efficient nitrogen fixation system, the total nitrogen content in a plant inoculated with the ammonium-secreting engineering bacterial strain was 40.6% higher than that of the control system, the contribution rate of biological nitrogen fixation was 21.5%, and the converted amount of biological nitrogen fixation was 0.8 g/plant. Assuming that there were 60,000 Zea mays L. plants per hectare, the amount of biological nitrogen fixation per hectare was estimated to be 48 kg, and the fertilizer saving rate was estimated to be about 25.6% according to the normal fertilization rate of 187.5 kg N/ha for Zea mays L. (Table 2).

In the control system, the contribution rate of biological nitrogen fixation was 10.1%, the converted amount of biological nitrogen fixation was about 0.23 g/plant, the amount of biological nitrogen fixation per hectare was estimated to be 13.8 kg, and the fertilizer saving rate was about 7.3% (Table 2).

Experimental Conclusion:

The artificial combined nitrogen fixation system constructed by the efficient nitrogen-fixing and ammonium-secreting microbial chassis and the efficient nitrogen utilization plant chassis can increase the biological nitrogen fixation efficiency and fixed nitrogen amount of a plant and is expected to achieve the optimal fertilizer-saving effect, where it is estimated that the combined nitrogen fixation system can reduce about 25.6% of the fertilizer consumption per hectare and the control system can reduce only 7.3% of the fertilizer consumption per hectare.

Example 4 the Use Effect of an Efficient Combined Nitrogen Fixation System Constructed by the Ammonium-Secreting Engineering Bacterial Strain and Oryza sativa L. In the Field Experimental Method (1) Determination of the Plant Growth Amount An experiment was conducted in a smart greenhouse in which the temperature and humidity could be controlled at all times. 5 treatment groups were set in the experiment (the ammonium-secreting engineering bacterial strain, the WT strain, the nifH gene-deleted mutant strain, 50 mg N of nitrogen application per kilogram of soil, and treatment control without fertilization and inoculation). 2 Oryza sativa L. varieties were adopted (efficient nitrogen utilization strain and control strain), and 8 replicates were set for each group in the experiment. A total of 5×2×8=80 samples were set in this experiment.

Oryza sativa L. seeds were soaked and washed in sterile water for 30 min, soaked in a 5% NaClO solution for 1 min, treated in 75% ethanol for 2 min, and washed 5 times with sterile water. The seeds obtained after the surface sterilization were soaked for 30 min in various prepared bacterial suspensions and a sterilized WT suspension (a control without inoculation), respectively. The soaked Oryza sativa L. seeds were placed in plastic pots (inner diameter: 20 cm, and height: 20 cm) each filled with 2 kg of a soil substrate (Klasmann-Deilmann) with 4 seeds per pot and 8 replicates per group. 8 replicates were set for each group. After the emergence of Oryza sativa L. seedlings, the thinning process was performed to reduce from 4 seedlings/pot to 2 seedlings/pot. The seedlings were managed in a growth cycle of Oryza sativa L. 60 days after the sowing, and the aboveground and underground growth amounts of Oryza sativa L. were measured.

Experimental Results:

On day 60 of the Oryza sativa L. growth cycle, aboveground and underground parts of a Zea mays L. plant were collected and tested for plant biomass, including plant height, plant weight, and root weight (Table 1). Data analysis showed that, compared with the fertilization and non-inoculation control systems, the combined nitrogen fixation system constructed by the Neb+amtR ammonium-secreting engineering bacterial strain and the Ham+hyg Oryza sativa L. strain had a significantly-increased plant biomass.

The plant height, biomasses of aboveground and underground parts, and total biomass of a plant in this efficient nitrogen fixation system were significantly higher than that in the control (Table 1). The total biomass of the plant inoculated with the ammonium-secreting engineering bacterial strain was 6.6% higher than that of the fertilization treatment and 10.9% higher than that of the non-inoculation control, where the biomass of the aboveground part was 10.4% higher than that of the fertilization treatment and 20.6% higher than that of the non-inoculation control. The root weight was 2.4% higher than that of the fertilization treatment and 2.6% higher than that of the non-inoculation control.

An average plant height in the artificially-designed efficient nitrogen fixation system was significantly higher than that in the control system (Table 1). An average plant height of Oryza sativa L. inoculated with the ammonium-secreting engineering bacterial strain was 4.3% higher than that of the fertilization treatment and 6.8% higher than that of the non-inoculation control.

Experimental Conclusion:

The artificial combined nitrogen fixation system constructed by the efficient nitrogen-fixing and ammonium-secreting microbial chassis and the efficient nitrogen utilization plant chassis can significantly increase a plant's growth amount and exhibit the optimal growth promotion effect on Oryza sativa L.

(2) Determination of an Amount of Biological Nitrogen Fixation by a $^{15}$N Stable Isotope Dilution Method Experimental Results:

The nitrogen-fixing ability of nitrogen-fixing bacteria in the artificially-designed combined rhizosphere nitrogen fixation system was evaluated by the 15N dilution method (Table 2). Data analysis of the artificial combined nitrogen fixation system constructed by the Neb+amtR ammonium-secreting engineering bacterial chassis and the Ham+hyg Oryza sativa L. chassis showed that, compared with the control system, the ammonium-secreting engineering bacteria significantly increased the total nitrogen content in an Oryza sativa L. plant, the percentage of nitrogen fixed from the air in the total nitrogen amount in a plant (biological nitrogen fixation efficiency), and the amount of biological nitrogen fixation.

In the efficient nitrogen fixation system, the total nitrogen content in a plant inoculated with the ammonium-secreting engineering bacterial strain was 48.2% higher than that of the control system, the contribution rate of biological nitrogen fixation was 18.5%, and the converted amount of biological nitrogen fixation was 0.14 g/plant. Assuming that there were 210,000 *Oryza sativa* L. plants per hectare, the amount of biological nitrogen fixation per hectare was estimated to be 29.4 kg, and the fertilizer saving rate was estimated to be about 24.5% according to the normal fertilization rate of 120 kg N/ha for *Oryza sativa* L. (Table 2).

In the control system, the contribution rate of biological nitrogen fixation was 9.0%, the converted amount of biological nitrogen fixation was about 0.06 g/plant, the amount of biological nitrogen fixation per hectare was estimated to be 12.6 kg, and the fertilizer saving rate was about 10.5% (Table 2).

Experimental Conclusion:

The artificial combined nitrogen fixation system constructed by the efficient nitrogen-fixing and ammonium-secreting microbial chassis and the efficient nitrogen utilization plant chassis can increase the biological nitrogen fixation efficiency and fixed nitrogen amount of a plant and is expected to achieve the optimal fertilizer-saving effect. It is estimated that the combined nitrogen fixation system can reduce about 24.5% of the fertilizer consumption per hectare and the control system can reduce only 10.5% of the fertilizer consumption per hectare.

Example 5 the Use Effect of an Efficient Combined Nitrogen Fixation System Constructed by the Ammonium-Secreting Engineering Bacterial Strain and *Triticum Aestivum* L. In the Field Experimental Method
(1) Determination of the Plant Growth Amount An Experiment was conducted in a smart greenhouse in which the temperature and humidity could be controlled at all times. 5 treatment groups were set in the experiment (the ammonium-secreting engineering bacterial strain, the WT strain, the nifH gene-deleted mutant strain, 50 mg N of nitrogen application per kilogram of soil, and treatment control without fertilization and inoculation). 2 *Triticum aestivum* L. varieties were adopted (efficient nitrogen utilization strain and control strain), and 8 replicates were set for each group in the experiment. A total of 5×2× 8=80 samples were set in this experiment.

*Triticum aestivum* L. seeds were soaked and washed in sterile water for 30 min, soaked in a 5% NaClO solution for 1 min, treated in 75% ethanol for 2 min, and washed 5 times with sterile water. The seeds obtained after the surface sterilization were soaked for 30 min in various prepared bacterial suspensions and a sterilized WT suspension (a control without inoculation), respectively. The soaked *Triticum aestivum* L. seeds were placed in plastic pots (inner diameter: 20 cm, and height: 20 cm) each filled with 2.5 kg of a soil substrate (Klasmann-Deilmann) with 4 seeds per pot and 8 replicates per group. 8 replicates were set for each group. Seedlings were managed in a growth cycle of *Triticum aestivum* L. 60 days after the sowing, and the aboveground and underground growth amounts of *Triticum aestivum* L. were measured.

Experimental Results:

On day 60 of the *Triticum aestivum* L. growth cycle, aboveground and underground parts of a *Triticum aestivum* L. plant were collected and tested for plant biomass, including plant height, plant weight, and root weight (Table 1). Data analysis showed that, compared with the fertilization and non-inoculation control systems, the combined nitrogen fixation system constructed by the Neb+amtR ammonium-secreting engineering bacterial strain and the Ham+NPT II *Triticum aestivum* L. strain had a significantly-increased plant biomass.

The plant height, biomasses of aboveground and underground parts, and total biomass of a plant in this efficient nitrogen fixation system were significantly higher than that in the control (Table 1). The total biomass of the plant inoculated with the ammonium-secreting engineering bacterial strain was 7.2% higher than that of the fertilization treatment and 14.9% higher than that of the non-inoculation control. The biomass of the aboveground part was 13.5% higher than that of the fertilization treatment and 19.0% higher than that of the non-inoculation control, and the root weight was 1.2% higher than that of the fertilization treatment and 3.6% higher than that of the non-inoculation control.

The average plant height in the artificially-designed efficient nitrogen fixation system was significantly higher than that in the control system (Table 1). The average plant height of *Triticum aestivum* L. inoculated with the ammonium-secreting engineering bacterial strain was 1.9% higher than that of the fertilization treatment and 4.7% higher than that of the non-inoculation control.

Experimental Conclusion:

The artificial combined nitrogen fixation system constructed by the efficient nitrogen-fixing and ammonium-secreting microbial chassis and the efficient nitrogen utilization plant chassis can significantly increase a plant's growth amount and exhibit the optimal growth promotion effect on *Triticum aestivum* L.

(2) Determination of an Amount of Biological Nitrogen Fixation by a 15N Stable Isotope Dilution Method Experimental Results:

The nitrogen-fixing ability of nitrogen-fixing bacteria in the artificially-designed combined rhizosphere nitrogen fixation system was evaluated by the $^{15}$N dilution method (Table 2). Data analysis of the artificial combined nitrogen fixation system constructed by the Neb+amtR ammonium-secreting engineering bacterial chassis and the Ham+NPT II *Triticum aestivum* L. chassis showed that, compared with the control system, the ammonium-secreting engineering bacteria significantly increased the total nitrogen content in a *Triticum aestivum* L. plant, the percentage of nitrogen fixed from the air in the total nitrogen amount in a plant (biological nitrogen fixation efficiency), and the amount of biological nitrogen fixation.

In the efficient nitrogen fixation system, the total nitrogen content in a plant inoculated with the ammonium-secreting engineering bacterial strain was 42.6% higher than that of the control system, the contribution rate of biological nitrogen fixation was 14.3%, the converted amount of biological nitrogen fixation was 0.02 g/plant, the amount of biological nitrogen fixation per hectare was 80 kg, and the fertilizer saving rate was about 66.6% (Table 2).

In the control system, the contribution rate of biological nitrogen fixation was 8.5%, and the converted amount of biological nitrogen fixation was about 0.01 g/plant. Assuming that there were 4,000,000 *Triticum aestivum* L. plants per hectare, the amount of biological nitrogen fixation per hectare was estimated to be 40 kg, and the fertilizer saving rate was estimated to be about 33.3% according to the normal fertilization rate of 120 kg N/ha for *Triticum aestivum* L. (Table 2).

Experimental Conclusion:

The artificial combined nitrogen fixation system constructed by the efficient nitrogen-fixing and ammonium-secreting microbial chassis and the efficient nitrogen utilization plant chassis can increase the biological nitrogen fixation efficiency and fixed nitrogen amount of a plant and is expected to achieve the optimal fertilizer-saving effect, where it is estimated that the combined nitrogen fixation system can reduce about 66.6% of the fertilizer consumption per hectare and the control system can reduce only 33.3% of the fertilizer consumption per hectare.

In Examples 3 to 5, measurement indexes of the experimental results included the plant growth amount and the amount of biological nitrogen fixation.

1. The plant growth amount included the plant height and weights of aboveground and underground parts, and relative growth rates of the plant height and the weights of aboveground and underground parts are shown in Table 1.

soil (concentration: 50 mg N per kg of soil), and the resulting mixture was thoroughly mixed for later use.

2. *Zea mays* L. (*Oryza sativa* L. or *Triticum aestivum* L.) seeds soaked in a bacterial solution were placed in the potting soil. 60 days after the sowing, the stems and leaves were collected, dried to a constant weight, ground, sieved through a 100-mesh sieve, and subjected to stable isotope ratio mass spectrometry analysis.

4 replicates were set for each group.

3. Calculation

1) A contribution rate of biological nitrogen fixation to plant nitrogen nutrition refers to a percentage of nitrogen fixed from the air to a total nitrogen amount of a plant (% Ndfa), and a calculation method is as follows:

$$\% Ndfa = (1 - \text{atom } \%^{15}NF \text{ excess}/\%^{15}NNF \text{ excess}) \times 100\%$$

where atom $\%^{15}NF$ excess refers to $^{15}N$ atom percent excess of a *Zea mays* L. (*Oryza sativa* L. or *Triticum aestivum* L.) plant inoculated with nitrogen-fixing bacteria; and atom $\%^{15}NNF$ excess refers to $^{15}N$ atom percent excess of a niH gene-mutant *Zea mays* L. (*Oryza sativa* L. or *Triticum aestivum* L.) plant.

A calculation result was expressed as an arithmetic mean value of 3 independent determination results obtained under repeated conditions.

TABLE 1

Growth rates of plant traits and biomasses of crops of the artificial combined rhizosphere nitrogen fixation system relative to the control system

| Artificial combined rhizosphere nitrogen fixation system | Growth rate relative to the fertilization control system (%) | | | | Growth rate relative to the non-inoculation control system (%) | | | |
|---|---|---|---|---|---|---|---|---|
| | Plant height | Aboveground part weight | Underground part weight | Total biomass | Plant height | Aboveground part weight | Underground part weight | Total biomass |
| Ammonium-secreting engineering bacterial strain + *Zea mays* L. | 1.9 ± 0.4 | 13.5 ± 1.6 | 1.2 ± 0.1 | 7.2 ± 1.0 | 4.7 ± 0.6 | 19.0 ± 1.8 | 3.6 ± 0.5 | 14.9 ± 0.6 |
| Ammonium-secreting engineering bacterial strain + *Oryza sativa* L. | 4.3 ± 1.0 | 10.4 ± 1.0 | 2.4 ± 0.2 | 6.6 ± 0.9 | 6.8 ± 0.4 | 20.6 ± 0.9 | 2.6 ± 0.1 | 10.9 ± 0.5 |
| Ammonium-secreting engineering bacterial strain + *Triticum aestivum* L. | 3.2 ± 0.3 | 11.2 ± 1.7 | 1.1 ± 0.2 | 6.3 ± 1.0 | 9.1 ± 0.7 | 15.7 ± 1.1 | 2.9 ± 0.3 | 7.8 ± 0.7 |

Note:
In the control system, nitrogen fertilizer was applied at an amount of 50 mg of nitrogen per kg of soil.

2. Determination of an Amount of Biological Nitrogen Fixation by a $^{15}N$ Stable Isotope Dilution Method The $^{15}N$ stable isotope dilution method is a general method for determining an amount of biological nitrogen fixation. In the present disclosure, the growth amounts and the amounts of biological nitrogen fixation of *Zea mays* L., *Oryza sativa* L., and *Triticum aestivum* L. were evaluated by basically the same methods. Specific operations and calculation methods were as follows:

1. Two weeks before the start of the experiment, 15N stable isotope-labeled ammonium sulfate was added to the 2) A total fixed nitrogen amount in a plant (N fixed) was expressed in grams and was calculated according to the following formula:

$$N\text{fixed} = Nt \times \%Ndfa \times \text{Biomass}$$

where

Nt refers to the total nitrogen content in a plant, %; and

Biomass refers to the sum of biomasses of aboveground and underground parts of a plant, g per plant.

The calculation result was expressed as an arithmetic mean value of 3 independent determination results obtained under repeated conditions.

Results are shown in Table 2.

TABLE 2

Calculated nitrogen contents and amounts of biological nitrogen fixation of crop plants in the artificially-designed combined rhizosphere nitrogen fixation system and control system

| | Total nitrogen content in a plant (%) | | Percentage of biologically-fixed nitrogen in a total nitrogen amount in a plant (%) | | The amount of biological nitrogen fixation (g/plant) | |
|---|---|---|---|---|---|---|
| | Artificial nitrogen fixation system | Control system | Artificial nitrogen fixation system | Control system | Artificial nitrogen fixation system | Control system |
| Ammonium-secreting engineering bacterial strain + *Zea mays* L. | 2.39 ± 0.26 | 1.70 ± 0.03 | 21.5 ± 1.0 | 10.1 ± 0.7 | 0.80 ± 0.020 | 0.23 ± 0.017 |
| Ammonium-secreting engineering bacterial strain + *Oryza sativa* L. | 1.23 ± 0.13 | 0.83 ± 0.05 | 18.5 ± 0.9 | 9.0 ± 0.5 | 0.14 ± 0.010 | 0.06 ± 0.008 |
| Ammonium-secreting engineering bacterial strain + *Triticum aestivum* L. | 3.98 ± 0.09 | 2.79 ± 0.06 | 14.3 ± 1.6 | 8.5 ± 0.8 | 0.02 ± 0.002 | 0.01 ± 0.001 |

What is claimed is:

1. An artificial combined rhizosphere nitrogen fixation system, comprising: a nitrogen-fixing and ammonium-secreting gene module constructed by a nitrogen-fixing microbial chassis and a nitrogen utilization module constructed by a non-leguminous plant chassis, wherein the nitrogen-fixing and ammonium-secreting gene module is a recombinant engineering bacterium comprising an artificially-designed nitrogen fixation activator Neb functional module and an artificially-designed amtR ammonium transport module, wherein the artificially-designed nitrogen fixation activator Neb functional module is encoded by the DNA sequence shown in SEQ ID NO: 1; and the artificially-designed amtR ammonium transport module is a gene with the DNA sequence shown in SEQ ID NO: 2; and the nitrogen utilization module constructed by the non-leguminous plant chassis is a recombinant plant comprising a synthetic ammonium-affiliated protein Ham, wherein the synthetic ammonium-affiliated protein Ham is encoded by the DNA sequence shown in SEQ ID NO: 3.

2. The artificial combined rhizosphere nitrogen fixation system according to claim 1, wherein the recombinant plant is one selected from the group consisting of:

recombinant *Zea mays* L. comprising the gene Ham and a gene bar;

recombinant *Oryza sativa* L. comprising the gene Ham and a gene hyg; and recombinant *Triticum aestivum* L. comprising the gene Ham and a gene NPT II.

3. A method of constructing the artificial combined rhizosphere nitrogen fixation system according to claim 1, the method comprising:
1) Introducing the nitrogen-fixing and ammonium-secreting gene module into a nitrogen-fixing microorganism to obtain a recombinant microorganism comprising the nitrogen-fixing and ammonium-secreting gene module; and
2) Introducing the nitrogen utilization module into different target plants to obtain different recombinant plants comprising the nitrogen utilization module.

4. A gene with the sequence shown in SEQ ID NO: 1, SEQ ID NO: 2, or SEQ ID NO: 3.

5. A plasmid, a vector, or an engineering bacterium comprising a gene with the sequence shown in SEQ ID NO: 1 and/or SEQ ID NO: 2.

6. A plasmid, a vector, or an engineering bacterium comprising a gene with the sequence shown in SEQ ID NO: 3.

7. A method of constructing a nitrogen-fixing and ammonium-secreting recombinant engineering bacterium, the method comprising the step of transforming a bacterium with a gene having the sequence shown in SEO ID NO: 1 and a gene having the sequence shown in SEQ ID NO: 2.

8. A method of constructing a recombinant plant for a nitrogen utilization, the method comprising the step of transforming a plant with a gene having the sequence shown in SEQ ID NO: 3.

9. A method of increasing plant biomass, the method comprising: inoculating a recombinant engineering bacterium constructed by the method according to claim 7 into a recombinant plant comprising a gene with the sequence shown in SEQ ID NO: 3.

10. The method according to claim 9, wherein the inoculating refers to a seed-coated inoculation at a rhizosphere of a crop.

* * * * *

SEQUENCE LISTING

<160> NUMBER OF SEQ ID NOS: 3

<210> SEQ ID NO 1
<211> LENGTH: 1000
<212> TYPE: DNA
<213> ORGANISM: Artificial Sequence
<220> FEATURE:
<223> OTHER INFORMATION: The sequence is synthetized.

<400> SEQUENCE: 1

```
atagacatca gctttgatac cggtgcgatt aggtacatga ttgtattatt tgcgcccgcc        60
gagcgcgcaa gtggcctata ccgttgcgtg cgccgggta tacaggtcat tgtggccccc       120
ttcatcgtta tggagtggcg tagctcaagg tgccgaggac gcgccgcgat taaagtctat       180
ggaaacgctc acgccgaacg ccaaaaatta tgcgcgtctg taaccaaaac gtggacttct       240
ctattccccc aactgcaatt cgggccgtcc ggtgcggata tagtgccgac agctgattgt       300
caacactccc gacgcgggat gcccgcatta gggtacaagc tgtttgaaac cccacaaggg       360
tcattccggc gcacaagccg cacaccacgt aatccttcca gtaataaatt tgatccaaca       420
tcttgcacga tagagcggaa agactaccgg gggccatgct ctcactacgc gcacactcaa       480
gtcacaacta atactgcgcg tcgcatgggg cgtttagcgt tcagctctac agctcagatg       540
tacgctatcc tcgcaaggcg accacgggga cgatcgactt tacaactgaa agagtcacgt       600
ccgctgaaaa acacccatcc cgctacagcg cgctcagtga tggtgataga gatgtcgact       660
tctttggtat gcacgggccg ttgcactcac aaaccttcag ccgataaacg cgcccacaaa       720
cccttgtcgg ttcgaggtgt gaaactagtg gtggagggga accgacaacc tgcctacccc       780
cgtgatgtgc cgtttccgca tcgattagat ttgaaaacta ggccttggac tgcaataagc       840
catggctcat tcatcaatac cgaacccgag caaggcggag ccctgaacgc ggacaaagcg       900
ttactccagc tgcaggatgt cactccacta gtcagacgaa actgctctca atcgaaacaa       960
gctggtattc tgttttacaa aatcaatcac gttcgactaa                            1000
```

<210> SEQ ID NO 2
<211> LENGTH: 800
<212> TYPE: DNA
<213> ORGANISM: Artificial Sequence

```
<220> FEATURE:
<223> OTHER INFORMATION: The sequence is synthetized.

<400> SEQUENCE: 2
cgtgtccaat ttgttcagcc ccgtgagttt ggtgcaacct actcggtcca aatgtgctgc      60
agaagcttaa gactctctcg gaagatgcgc gcatgctcag tgggaatccc tcacatgccc     120
tctgtcgcac cacacgatat taaaatcctc gccttcacgc gtgggttaca atatagttgg     180
ggaacctctc tgcatcgatg gattaaactc accaatgtgt taaacagaaa tctgacccga     240
gtactggctg ttaacccgat aaatttcgag gcttgcctta cacaaatttt acatcggata     300
agccgcaaag tgcaccccgt gcgcagactg attataaaat tgatcgggat gcaacgacag     360
tggttcttca ctgggggcac acgtttgact tctagtgttc gtgcttttc  catgaaagca     420 ttattacgac gggctttgtt attagatgct tcacctctga tagcccagta cgggtttagg     480 aaggggcac  gccccacaca aatccacgga gtctcacccg atcatgatcc tcgtatttgg     540 taccectggg gtcaacctcc agtagattca aaatgtagcg agtgtagctt tataggtggt     600
tcctgtaaca tattaagttg cgtgggagcg aaaaattccc tagtaggtca tcctgctgag     660
ccgggaagtg atctcaccaa tatatcaggg ggccttccga gcacgtggag ggttcttccg     720
gggggaagtc cgagcccctt cgctaggcta ggttcctctt tcgataactc cgcccaacac     780
gtagtcgcat gtatttggtc                                                  800

<210> SEQ ID NO 3
<211> LENGTH: 471
<212> TYPE: DNA
<213> ORGANISM: Artificial Sequence
<220> FEATURE:
<223> OTHER INFORMATION: The sequence is synthetized.

<400> SEQUENCE: 3
gcattcctga tatgcgaggt ccgaacaccc tggtttacgg catggaggct aggtccctac      60
gttctggtct actgtaaggc acgttatgca tcatgcggcc cccccgcgag ctgcgatacg     120
ccttttacaa tagaaatgaa taaaaaatgc catgttggcg aacggctgag actggcacac     180
gcctgctacc cgaagaacac agatctaatt ttgcctgttg tgatgctagg cttgattgat     240
tcatcgttga caggtctgac ctttacgatg tgttcctttt cccggatccc acagaggctc     300
cagttagtgc cttaccattt catcaacgcc ctatactatc tggttcttaa tccaggtttc     360
agaaggaggg ggcgaccgat cctaccttca ccgctagcgc ccagccgcaa atgtaaacgt     420
tcgtgcggac ttagccgtct acgagaaggc actagtgtag acaacaattt g              471
```